(12) United States Patent
Gonzalez et al.

(10) Patent No.: US 7,402,387 B2
(45) Date of Patent: *Jul. 22, 2008

(54) METHODS AND COMPOSITIONS FOR DETECTING DIHYDROPYRIMIDINE DEHYDROGENASE SPLICING MUTATIONS

(75) Inventors: Frank J. Gonzalez, Bethesda, MD (US); Pedro Fernandez-Salguero, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 280 days.

This patent is subject to a terminal disclaimer.

(21) Appl. No.: 10/911,237

(22) Filed: Aug. 3, 2004

(65) Prior Publication Data

US 2005/0136433 A1    Jun. 23, 2005

Related U.S. Application Data

(63) Continuation of application No. 09/308,080, filed as application No. PCT/US97/04269 on Mar. 19, 1997, now Pat. No. 6,787,306.

(60) Provisional application No. 60/013,835, filed on Mar. 20, 1996.

(51) Int. Cl.
| | |
|---|---|
| C12Q 1/68 | (2006.01) |
| G01N 33/48 | (2006.01) |
| C12N 9/02 | (2006.01) |
| C12N 15/00 | (2006.01) |
| C12P 19/34 | (2006.01) |
| C12Q 1/32 | (2006.01) |
| C07H 21/00 | (2006.01) |
| C07K 14/00 | (2006.01) |

(52) U.S. Cl. .......... 435/6; 435/189; 435/320.1; 435/91.2; 435/26; 536/23.1; 536/23.2; 536/23.5; 530/350; 436/94

(58) Field of Classification Search .......... 435/189, 435/320.1, 91.2, 26, 6; 536/23.1, 23.2, 23.5; 530/350; 436/94
See application file for complete search history.

(56) References Cited

U.S. PATENT DOCUMENTS 5,856,454 A   1/1999   Gonzalez et al.

FOREIGN PATENT DOCUMENTS

| WO | WO 95/28489 A1 | 10/1995 |
|---|---|---|
| WO | WO 97/35034 A1 | 9/1997 |

OTHER PUBLICATIONS

Zgombic-Knight et al., J. Biol. Chem. 270(9):4305-4311; 1996.*
Guo et al., Nucleic Acid Research 22(24):5456-5465, 1994.*
Gonzalez, F. et al., "Diagnostic analysis, clinical importance and molecular basis of dihydropyrimidine dehydrogenase deficiency," *TiPS*, 16:325-327 (1995).
Hiroshi Y. et al. "cDNA cloning and chromosome mapping of human dihydropyrimidine dehydrogenase, an enzyme associated with 5-flourouracil toxicity and congenital thymine uraciluria," *J. Biol. Chem.*, vol. 269, pp. 23192-23196 (1994).
Kuilenburg, Andre B.P. et al.: "Lethal outcome of a patient with a complete dihydropyrimidine dehydrogenase (DPD) deficiency after administration of 5-fluorouracil: frequency of the common IVS14+1G>A mutation causing DPD Deficiency"; *Clinical Cancer Research*, vol. 7; pp. 1149-1153; May 2001.
Kuivaniemi, Helena et al.: "Identical G+1 to A mutations in three different introns of the Type III procollagene gene (COL3A1) produce different patterns of RNA splicing in three variants ot Ehlers-Danlos Syndrome IV"; *J. Biological Chem.*, vol. 265, No. 20; pp. 12067-12074; Jul. 15, 1990.
Marvit, J. et al: "GT to AT transition at a splice donor site causes skipping of the preceeding exon in penylketonuria," *Nucleic Acids Research*, vol. 15, No. 14, pp. 5613-5628, (1987).
Meinsma, R. et al., "Human Polymorphism in Drug Metabolism: Mutation in the Dihydropyrimidine Dehydrogenase Gene Results in Exon Skipping and Thymine Uracilurea," *DNA & Cell. Biol.*, 14(1)1-6 (1995).
Roy et al., "Molecular scanning of human diseases," *Singapore J. of Obstetrics and Gyn.*, vol. 26, No. 3, pp. 176-186, (Nov. 1995).
Vreken, P. et al., "A point mutation in an invariant splice donor site leads to exon skipping in two unrelated Dutch patients with dihydropyrimidine dehydrogenase deficiency," *J. Inherit. Metab. Dis.*, 19(5):645-54 (1996).
Wei, X. et al. "Molecular Basis of the Human Dihydropyrimidine Dehydrogenase Deficicency and 5-Fluorouracil Toxicity," *J. Clin. Invest.*, 98(3)610-615 (1996).
Yokota, Hiroshi et al.: "cDNA cloning and chromosome mapping of human dihydropyrimidine dehydrogenase, and enzyme associated with 5-flouorouracil toxicity and congenital thymine uracilura"; J. Biological Chemistry, vol. 269, No. 37; pp. 23192-23196 (Sep. 16, 1994).
OMIM Entry for "Dyhydropyrimidine Dehydrogenase; DPYD" printed on Dec. 3, 2003.

* cited by examiner

*Primary Examiner*—Delia M Ramirez
(74) *Attorney, Agent, or Firm*—Townsend and Townsend and Crew LLP (57) ABSTRACT

The present invention provides compositions, methods, and kits for the detection of genetic polymorphisms or mutations of the dihydropyrimidine dehydrogenase deficiency (DPDD). The polymorphisms or mutations generally occur in the dihydropyrimidine dehydrogenase (DPD) gene in chromosome 1. Also provided are mutant forms of DPD.

11 Claims, 4 Drawing Sheets

```
1                                                                    50
TGTTAATGAA GATAAATATT TTTGTTTTTT CGCTGTTCTA AACCTAGGGT
ACAATTACTT CTATTTATAA AAACAAAAAA GCGACAAGAT TTGGATCCCA 51                                                                   100
TACAAGAAGT AATTTATCTG GAGCTAACAA ATACTTTATT TTACCTTTTT
ATGTTCTTCA TTAAATAGAC CTCGATTGTT TATGAAATAA AATGGAAAAA 101                                                                  150
ATTTGCAAGT AGTTTATGTT CAATTCTAAT TTAATGTATA TTAAAAATTC
TAAACGTTCA TCAAATACAA GTTAAGATTA AATTACATAT AATTTTTAAG 151                                                                  200
    5'    PRIMER DELF1              3'
CTCTGCAAAT ATGTGAGGAG GGACCTCATA AAATATTGTC ATATGGAAAT
GAGACGTTTA TACACTCCTC CCTGGAGTAT TTTATAACAG TATACCTTTA 201                                                                  250
GAGCAGATAA TAAAGATTAT AGCTTTTCTT TGTCAAAAGG AGACTCAATA
CTCGTCTATT ATTTCTAATA TCGAAAAGAA ACAGTTTTCC TCTGAGTTAT 251                                                         295
TCTTTACTCT TTCATGAG GAC ATT GTG ACA AAT GTT TCC CCC AGA
AGAAATGAGA AAGTAGTC CTG TAA CAC TGT TTA CAA AGG GGG TCT
                  D   I   V   T   N   V   S   P   R
                      5'                         3'

296                                                         337
ATC ATC CGG GGA ACC ACC TCT GGC CCC ATG TAT GGC CCT GGA
TAG TAG GCC CCT TGG TGG AGA CCG GGG TAC ATA CCG GGA CCT
 I   I   R   G   T   T   S   G   P   M   Y   G   P   G 338                                                         379
CAA AGC TCC TTT CTG AAT ATT GAG CTC ATC AGT GAG AAA ACG
GTT TCG AGG AAA GAC TTA TAA CTC GAG TAG TCA CTC TTT TGC
 Q   S   S   F   L   N   I   E   L   I   S   E   K   T 380                                                         421
GCT GCA TAT TGG TGT CAA AGT GTC ACT GAA CTA AAG GCT GAC
CGA CGT ATA ACC ACA GTT TCA CAG TGA CTT GAT TTC CGA CTG
 A   A   Y   W   C   Q   S   V   T   E   L   K   A   D
                      3'                            5'
```

*FIG. 1A.*

```
422                Mae II                                            470
TTC CCA GAC AAC  G T AAGTG TGATAAAAAT CTAAAACAAG AGAATTGGCA
AAG GGT CTG TTG  C A TTCAC ACTATTTTA GATTTGTTC TCTTAACCGT
 F   P   D   N    X
```

```
471                                                                  520
TAAGTTGGTG AATGTTTATT TAAACATCCA ATTCATAGGC TTATAAATAT
ATTCAACCAC TTACAAATAA ATTTGTAGGT TAAGTATCCG AATATTTATA
```

```
521                                                                  570
TAATGTGTAT ATTTTATCAA CGAATCTGCC AGTTGCTTTG CTGATGCATA
ATTACACATA TAAAATAGTT GCTTAGACGG TCAACGAAAC GACTACGTAT
                          3' PRIMER DELR1              5'
```

```
571                                                                  620
GAAAGATAAA AAAGAAAGAA AAGCTCAAGA ACTCATAAAA ACCCACACAA
CTTTCTATTT TTTCTTTCTT TTCGAGTTCT TGAGTATTTT TGGGTGTGTT
```

```
621                                                                  670
TGTGAAGCTC TGTTATAAAT GGGTGCCATG TAAGATGGAA GAAGTATCTA
ACACTTCGAG ACAATATTTA CCCACGGTAC ATTCTACCTT CTTCATAGAT
```

```
671                                                                  720
CATAAGCAGA AGGAAGAGAA ATGAAATACT CATTTTATTG AGTTGGCCCC
GTATTCGTCT TCCTTCTCTT TACTTTATGA GTAAAATAAC TCAACCGGGG
```

```
721                                                                  770
CACTGTATGT GGCTGGTATT TATGAAGGTG ATGACCCAGG AAGAAATTGT
GTGACATACA CCGACCATAA ATACTTCCAC TACTGGGTCC TTCTTTAACA
```

```
771                                                                  820
AAACTATAAA CCACTCCAAA TATAAACCCG AGGCAGAAGC AGCATATCTC
TTTGATATTT GGTGAGGTTT ATATTTGGGC TCCGTCTTCG TCGTATAGAG
```

```
821                                             861
CTATGAAGCC TGTATTTACT CAGTGGGAAA TAATTTATTA A
GATACTTCGG ACATAAATGA GTCACCCTTT ATTAAATAAT T
```

*FIG. 1B.*

5' TGTTAATGAAGATAAATATTTTTATTTTTGCGCTATTCTAAACCTAGAGTTAC

AAGAAGTAATTTATCTGGAGCTAACAAATACTTTATTTTACCTTTTTATTTGCAA

5' TGCAAATATG
GTAGTTTATGTTCAATTCTAATTTAATGTATATTAAAAATTCCTCTGCAAATATG

TGAGGAGGGACC 3'
TGAGGAGGGACCTCATAAATATTGTCATATGGAGATGAGCAGATAATAAAGA

TTATAGCTTTTCTTTGTCAAAAGGAGACTCAATATCTTTACTCTTTCATCAG<u>GA</u>

<u>CATTGTGACAAATGTTTCCCCCAGAATCATCCGGGGAACCACCTCTGGCCC</u>

<u>CATGTATGGCCCTGGACAAAGCTCCTTTCTGAATATTGAGCTCATCAGTGAG</u>

<u>AAAACGGCTGCATATTGGTGTCAAAGTGTCACTGAACTAAAGGCTGACTTCC</u>

<u>CAGACAACG</u>T AAGTGTGATAAAAATCTAAACAAGAGAATTGGCATAAGTT

GGTGAATGTTTATTTAAACATCCAATTCATAGGCTTATAAATATTAATGTGTATA

3' CTTAGACGGTCAACGAAACGAC 5'
TTTTATCAAAGAATCTGCCAGTTGCTTTGCTGATGCATAGAAAGATAAAAAG

AAAGAAAAGCTCAAGAACTCATAAAAACCCACACAATGTGAAGCTCGTTATA

AATGGGTGCCATGTAAGATGGAAGAAGTATCTACATAAGCAGAAGGAAGAGA

AATGAAATACTCAATTTATTGAGTTGGCCCCCACTGTATGTGGCTGGCATTTA

TGAAGGTGATGACCCAGGAAGAAATTGTCACCTATAAATCATCCAAATATCC

CGAGGCAGAAGCAGCATCTCTCCTATGAAGTCTGTATTTATTTCAGCGGGAA

ATAATTTATTA 3'

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
    (A) LENGTH: 861 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: CDS
    (B) LOCATION: 269..433
    (D) OTHER INFORMATION: /note= "dihydropyrimidine dehydrogenase
    (DPD) gene region of splicing mutant
        mRNA encoding amino acids 581-635"

(ix) FEATURE:
    (A) NAME/KEY: mutation
    (B) LOCATION: replace(434, "a")
    (D) OTHER INFORMATION: /note= "G -> A mutation at 3' donor
        splice junction consensus sequence
        leading to loss of exon in DPD mRNA
        and DPD deficiency"

(xi) SEQUENCE DESCRIPTION: SEQ ID NO: 1:

```
TGTTAATGAA GATAAATATT TTTGTTTTTT CGCTGTTCTA AACCTAGGGT TACAAGAAGT      60

AATTTATCTG GAGCTAACAA ATACTTTATT TTACCTTTTT ATTTGCAAGT AGTTTATGT     120

CAATTCTAAT TTAATGTATA TTAAAAATTC CTCTGCAAAT ATGTGAGGAG GGACCTCAT     180

AAATATTGTC ATATGGAAAT GAGCAGATAA TAAAGATTAT AGCTTTTCTT TGTCAAAAG     240

AGACTCAATA TCTTTACTCT TTCATGAG GAC ATT GTG ACA AAT GTT TCC CCC        292
                               Asp Ile Val Thr Asn Val Ser Pro
                                1                   5

ATA ATC ATC CGG GGA ACC ACC TCT GGC CCC ATG TAT GGC CCT GGA CAA       340
Ile Ile Ile Arg Gly Thr Thr Ser Gly Pro Met Tyr Gly Pro Gly Gln
     10                  15                  20

AGC TCC TTT CTG AAT ATT GAG CTC ATC AGT GAG AAA ACG GCT GCA TAT       388
Ser Ser Phe Leu Asn Ile Glu Leu Ile Ser Glu Lys Thr Ala Ala Tyr
 25                  30                  35                  40

TGG TGT CAA AGT GTC ACT GAA CTA AAG GCT GAC TTC CCA GAC AAC           433
Trp Cys Gln Ser Val Thr Glu Leu Lys Ala Asp Phe Pro Asp Asn
                 45                  50                  55

GTAAGTGTGA TAAAAATCTA AAACAAGAGA ATTGGCATAA GTTGGTGAAT GTTTATTTA     493
```

-continued

```
ACATCCAATT CATAGGCTTA TAAATATTAA TGTGTATATT TTATCAACGA ATCTGCCAG        553

TGCTTTGCTG ATGCATAGAA AGATAAAAAA GAAAGAAAAG CTCAAGAACT CATAAAAAC        613

CACACAATGT GAAGCTCTGT TATAAATGGG TGCCATGTAA GATGGAAGAA GTATCTACA        673

AAGCAGAAGG AAGAGAAATG AAATACTCAT TTTATTGAGT TGGCCCCCAC TGTATGTGG        733

TGGTATTTAT GAAGGTGATG ACCCAGGAAG AAATTGTAAA CTATAAACCA CTCCAAATA        793

AAACCCGAGG CAGAAGCAGC ATATCTCCTA TGAAGCCTGT ATTTACTCAG TGGGAAATA        853

TTTATTAA                                                                861
```

(2) INFORMATION FOR SEQ ID NO: 2:

(i) SEQUENCE CHARACTERISTICS:
        (A) LENGTH: 55 amino acids
        (B) TYPE: amino acid
        (D) TOPOLOGY: linear     (ii) MOLECULE TYPE: protein         (xi) SEQUENCE DESCRIPTION: SEQ ID NO: 2:

```
Asp Ile Val Thr Asn Val Ser Pro Ile Ile Ile Arg Gly Thr Thr Ser
 1               5                  10                  15

Gly Pro Met Tyr Gly Pro Gly Gln Ser Ser Phe Leu Asn Ile Glu Leu
            20                  25                  30

Ile Ser Glu Lys Thr Ala Ala Tyr Trp Cys Gln Ser Val Thr Glu Leu
        35                  40                  45

Lys Ala Asp Phe Pro Asp Asn
        50                  55
```

(2) INFORMATION FOR SEQ ID NO: 3:

(i) SEQUENCE CHARACTERISTICS:
        (A) LENGTH: 22 base pairs
        (B) TYPE: nucleic acid
        (C) STRANDEDNESS: single
        (D) TOPOLOGY: linear     (ii) MOLECULE TYPE: DNA     (ix) FEATURE:
        (A) NAME/KEY: -
        (B) LOCATION: 1..22
        (D) OTHER INFORMATION: /note= "primer DELF1 (forward)"

(xi) SEQUENCE DESCRIPTION: SEQ ID NO: 3:

```
TGCAAATATG TGAGGAGGGA CC                                                 22
```

(2) INFORMATION FOR SEQ ID NO: 4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear     (ii) MOLECULE TYPE: DNA     (ix) FEATURE:
        (A) NAME/KEY: -
        (B) LOCATION: 1..22
        (D) OTHER INFORMATION: /note= "primer DELR1 (reverse)"

(xi) SEQUENCE DESCRIPTION: SEQ ID NO: 4:

```
CAGCAAAGCA ACTGGCAGAT TC                                                 22
```

(2) INFORMATION FOR SEQ ID NO: 5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear     (ii) MOLECULE TYPE: DNA     (ix) FEATURE:
        (A) NAME/KEY: -
        (B) LOCATION: 1..18
        (D) OTHER INFORMATION: /note= "primer DPD15F (forward)"

(xi) SEQUENCE DESCRIPTION: SEQ ID NO: 5:

```
TTGTGACAAA TGTTTCCC                                              18
```

(2) INFORMATION FOR SEQ ID NO: 6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear     (ii) MOLECULE TYPE: DNA     (ix) FEATURE:
        (A) NAME/KEY: -
        (B) LOCATION: 1..24
        (D) OTHER INFORMATION: /note= "primer DPD15R (reverse)"

(xi) SEQUENCE DESCRIPTION: SEQ ID NO: 6:

```
AGTCAGCCTT TAGTTCAGTG ACAC                                       24
```

(2) INFORMATION FOR SEQ ID NO: 7:

(i) SEQUENCE CHARACTERISTICS:
        (A) LENGTH: 856 base pairs
        (B) TYPE: nucleic acid
        (C) STRANDEDNESS: single
        (D) TOPOLOGY: linear     (ii) MOLECULE TYPE: DNA     (xi) SEQUENCE DESCRIPTION: SEQ ID NO: 7:

```
TGTTAATGAA GATAAATATT TTTATTTTTG CGCTATTCTA AACCTAGAGT TACAAGAAGT    60

AATTTATCTG GAGCTAACAA ATACTTTATT TTACCTTTTT ATTTGCAAGT AGTTTATGT    120

CAATTCTAAT TTAATGTATA TTAAAAATTC CTCTGCAAAT ATGTGAGGAG GGACCTCAT    180

AAATATTGTC ATATGGAGAT GAGCAGATAA TAAAGATTAT AGCTTTTCTT TGTCAAAAG    240

AGACTCAATA TCTTTACTCT TTCATCAGGA CATTGTGACA AATGTTTCCC CCATAATCA    300

CCGGGGAACC ACCTCTGGCC CCATGTATGG CCCTGGACAA AGCTCCTTTC TGAATATTG    360

GCTCATCAGT GAGAAAACGG CTGCATATTG GTGTCAAAGT GTCACTGAAC TAAAGGCTG    420

CTTCCCAGAC AACGTAAGTG TGATAAAAAT CTAAACAAG AGAATTGGCA TAAGTTGGT     480

AATGTTTATT TAAACATCCA ATTCATAGGC TTATAAATAT TAATGTGTAT ATTTTATCA    540

AGAATCTGCC AGTTGCTTTG CTGATGCATA GAAAGATAAA AAGAAAGAA AAGCTCAAG     600

ACTCATAAAA ACCCACACAA TGTGAAGCTC GTTATAAATG GGTGCCATGT AAGATGGAA    660

AAGTATCTAC ATAAGCAGAA GGAAGAGAAA TGAAATACTC AATTTATTGA GTTGGCCCC    720

ACTGTATGTG GCTGGCATTT ATGAAGGTGA TGACCCAGGA AGAAATTGTC ACCTATAAA    780
```

-continued

```
CATCCAAATA TCCCGAGGCA GAAGCAGCAT CTCTCCTATG AAGTCTGTAT TTATTTCAG       840

GGGAAATAAT TTATTA                                                     856
```

METHODS AND COMPOSITIONS FOR DETECTING DIHYDROPYRIMIDINE DEHYDROGENASE SPLICING MUTATIONS

TECHNICAL FIELD OF THE INVENTION

The present invention relates to methods and compositions for detecting splicing defects in the dihydropyrimidine dehydrogenase gene. The methods and compositions are useful for identifying persons who are at risk of a toxic reaction to the commonly employed cancer chemotherapy agent, 5-fluorouracil.

BACKGROUND OF THE INVENTION

5-Fluorouracil (5-FU) is commonly used in the treatment of cancers, including cancers of the breast, head, neck, and digestive system. The efficacy of 5-FU as a cancer treatment varies significantly among patients. Clinically significant differences in systemic clearance and systemic exposure of 5-FU are often observed. See, Grem, J. L. In Chabner, B. A. and J. M. Collins (eds.), *Cancer Chemotherapy: Principles and Practice*, pp. 180-224, Philadelphia, Pa., Lippincott, 1990). Furthermore, 5-FU treatment is severely toxic to some patients, and has even caused death. See, Fleming et al. (1993) *Eur. J. Cancer* 29A: 740-744; Thyss et al. (1986) *Cancer Chemother. Pharmacol.* 16: 64-66; Santini et al. (1989) *Br. J. Cancer* 59: 287-290; Goldberg et al. (1988) *Br. J. Cancer* 57: 186-189; Trump al. (1991) *J. Clin. Oncol.* 9: 2027-2035; and Au et al. (1982) *Cancer Res.* 42: 2930-2937.

Patients in whom 5-FU is severely toxic typically have low levels of dihydropyrimidine dehydrogenase (DPD) activity. See, Tuchman et al. (1985) *N. Engl. J. Med.* 313: 245-249; Diasio et al. (1988) *J. Clin. Invest.* 81: 47-51; Fleming et al. (1991) *Proc. Am. Assoc. Cancer Res.* 32: 179; Harris et al. (1991) *Cancer* (Phila.) 68: 499-501; Houyau et al. (1993) *J. Nat'l Cancer Inst.* 85: 1602-1603; Lyss et al. (1993) *Cancer Invest.* 11: 239-240. Dihydropyrimidine dehydrogenase (DPD, EC 1.3.1.2) is the principal enzyme involved in the degradation of 5-FU, which acts by inhibiting thymidylate synthase. See, Heggie et al. (1987) *Cancer Res.* 47: 2203-2206; Chabner et al. (1989) In DeVita et al. (eds.), *Cancer—Principles and Practice of Oncology*, pp. 349-395, Philadelphia, Pa., Lippincott; Diasio et al. (1989) *Clin. Pharmacokinet.* 16: 215-237; Grem et al., supra. The level of DPD activity also affects the efficacy of 5-FU treatments, as 5-FU plasma levels are inversely correlated with the level of DPD activity. See, Iigo et al. (1988) *Biochem. Pharm.* 37: 1609-1613; Goldberg et al., supra.; Harris et al., supra.; Fleming et al., supra. In turn, the efficacy of 5-FU treatment of cancer is correlated with plasma levels of 5-FU.

In addition to its 5-FU degrading activity, DPD is also the initial and rate limiting enzyme in the three-step pathway of uracil and thymine catabolism, leading to the formation of β-alanine and β-aminobutyric acid, respectively. See, Wasternack et al. (1980) *Pharm. Ther.* 8: 629-665. DPD deficiency is associated with inherited disorders of pyrimidine metabolism, clinically termed thymine-uraciluria. See, Bakkeren et al. (1984) *Clin. Chim. Acta.* 140: 247-256. Clinical symptoms of DPD deficiency include a nonspecific cerebral dysfunction, and DPD deficiency is associated with psychomotor retardation, convulsions, and epileptic conditions. See, Berger et al. (1984) *Clin. Chim. Acta* 141: 227-234; Wadman et al. (1985) *Adv. Exp. Med. Biol.* 165A: 109-114; Wilcken et al. (1985) *J. Inhert. Metab. Dis.* 8 (Suppl. 2): 115-116; van Gennip et al. (1989) *Adv. Exp. Med. Biol.* 253A: 111-118; Brockstedt et al. (1990) *J. Inherit. Metab. Dis.* 12: 121-124; and Duran et al. (1991) *J. Inherit. Metab. Dis.* 14: 367-370. Biochemically, patients having DPD deficiency have an almost complete absence of DPD activity in fibroblasts (see, Bakkeren et al., supra) and in lymphocytes (see, Berger et al., supra and Piper et al. (1980) *Biochim. Biophys. Acta* 633: 400-409. These patients typically have a large accumulation of uracil and thymine in their cerebrospinal fluid (see, Bakkeren et al., supra.) and urine (see, Berger et al., supra.; Bakkeren et al., supra.; Brockstedt et al., supra.; and Fleming et al. (1992) *Cancer Res.* 52: 2899-2902).

Familial studies suggest that DPD deficiency follows an autosomal recessive pattern of inheritance. See, Diasio et al., (1988) supra. Up to three percent of the general human population are estimated to be putative heterozygotes for DPD deficiency, as determined by enzymatic activity in lymphocytes. See, Milano and Eteinne (1994) *Pharmacogenetics*. This suggests that the frequency of homozygotes for DPD deficiency may be as high as one person per thousand.

DPD has been purified from liver tissue of rats (see, Shiotani and Weber (1981) *J. Biol. Chem.* 256: 219-224; Fujimoto et al. (1991); *J. Nutr. Sci. Vitaminol.* 37: 89-98], pig [Podschun et al. (1989) *Eur. J. Biochem.* 185: 219-224), cattle (see, Porter et al. (1991) *J. Biol. Chem.* 266: 19988-19994), and humans (see, Lu et al. (1992) *J. Biol. Chem.* 267: 1702-1709). The pig enzyme contains flavins and iron-sulfur prosthetic groups and exists as a homodimer with a monomer Mr of about 107,000 (see, Podschun et al., supra.). Since the enzyme exhibits a nonclassical two-site ping-pong mechanism, it appears to have distinct binding sites for NADPH/NADP and uracil/5,6-dihydrouracil (see, Podschun et al. (1990) *J. Biol. Chem.* 265: 12966-12972). An acid-base catalytic mechanism has been proposed for DPD (see, Podschun et al. (1993) *J. Biol. Chem.* 268: 3407-3413).

The DPD cDNA is described in copending U.S. application Ser. No. 08/304,309. Recently, DPD mRNA from patients lacking dihydrompyrimidine activity was found to lack an exon which encodes a 165 base pair sequence found in the wild-type DPD cDNA. See, Meinsma et al. (1995) *DNA and Cell Biology* 14(1): 1-6.

Because an undetected DPD deficiency poses a significant danger to a cancer patient who is being treated with 5-FU, a great need exists for a simple and accurate test for DPD deficiency. Such a test will also facilitate diagnosis of disorders that are associated with DPD deficiency, such as uraciluria. The present invention provides such a test, thus fulfilling these and other needs.

SUMMARY OF THE INVENTION

Particular mutations in the dihydropyrimidine dehydrogenase gene are described herein which lead to loss of dihydropyrimidine dehydrogenase activity. The mutations result in the loss of a fraament of the protein encoded by the gene due to a splicing defect, wherein said fraament consists of SEQ ID NO: 2. The splicing defect results in the loss of an exon encoding the amino acid sequence of SEQ ID NO: 2. The assays and compositions of the invention detect the splicing defect in the genomic DNA which results in the loss of the exon.

A variety of assays for detecting splicing defect mutations in patients are provided. The assays determine whether RNA encoded by genomic DNA is competent to be spliced to produce mRNA with nucleic acids encoding the exon which corresponds to the amino acid sequence of SEQ ID NO:2. For example, sequencing, PCR, LCR, and oligonucleotide array based assays are used to detect the mutations.

In one class of embodiments, the methods comprise the step of determining whether a nucleic acid encoding an mRNA for the dihydropyrimidine dehydrogenase gene has an exon corresponding to the amino acid sequence of SEQ ID NO:2. This determination is performed in sequencing, PCR, LCR, and oligonucleotide array based hybridization assays. For example, in one class of PCR based assays, the intronic genomic DNA encoding the dihydropyrimidine dehydrogenase in the region flanking the exon which encodes the amino acid sequence of SEQ ID NO:2 is hybridized to a set of PCR primers for amplification and analysis of the intron exon splice boundaries.

Example primers which are used for amplifying the splice regions include DELF1 and DELR1. Similar primers which hybridize to the same sites, or to sites proximal to the primer binding sites are also used.

One particular mutation which results in an abnormal dihydropyrimidine dehydrogenase gene phenotype is the conversion of a G to an A residue at the 3' GT splice site of the exon which encodes the amino acid sequence of SEQ ID NO:2 of the corresponding wild-type protein. The 3' wild-type splice site is recognized by restriction endonucleases which recognize the Mae II cleavage site. The ability of the cleavage site to be cleaved by restriction endonucleases which recognize the Mae II site is used to distinguish wild-type from abnormal dihydropyrimidine dehydrogenase genomic DNAs. For example, a region including the mutation is amplified by PCR, and the PCR products cleaved by Mae II. This results in the cleavage of nucleic acids amplified by the wild-type gene, but mutant sequences are not amplified.

In addition to PCR detection methods, nucleic acid arrays are used to discriminate single base-pair mismatches, or to directly sequence DNA by hybridization to arrays. The sequence of the splice site is also determined by standard or PCR sequencing of the site, e.g., using primers which flank the site in a pol I or taq PCR based sequencing assay.

In addition to methods and compositions for abnormal dihydropyrimidine dehydrogenase gene detection, the invention provides kits for practicing the methods. Typically, the kit contains a first PCR primer which binds to DNA 3' of a splice site in the genomic DNA for dihydropyrimidine dehydrogenase gene for an exon encoding the amino acid sequence of SEQ ID NO:2, and a second PCR primer which binds to DNA 5' of a splice site in the genomic DNA for dihydropyrimidine dehydrogenase gene for an exon encoding the amino acid sequence of SEQ ID NO:2. The kit optionally contains other components such as instructions for the detection of an abnormal dihydropyrimidine dehydrogenase gene, restriction enzymes such as Mae II, PCR or other in vitro amplification reagents (buffers, enzymes, salts and the like), oligonucleotide array detection chips and the like.

DETAILED DESCRIPTION OF THE DRAWING

DEFINITIONS

Unless defined otherwise, all technical and scientific terms used herein have the same meaning as commonly understood by one of ordinary skill in the art to which this invention belongs. Singleton et al. (1994) Dictionary of Microbiology and Molecular Biology, second edition, John Wiley and Sons (New York); Walker (ed) (1988) The Cambridge Dictionary of Science and Technology, The press syndicate of the University of Cambridge, NY; and Hale and Marham (1991) The Harper Collins Dictionary of Biology Harper Perennial, NY provide one of skill with a general dictionary of many of the terms used in this invention. Although any methods and materials similar or equivalent to those described herein can be used in the practice or testing of the present invention, preferred methods and materials are described. For purposes of the present invention, the following terms are defined below.

The term "nucleic acid" refers to deoxyribonucleotides, ribonucleotides, and polymers thereof in either single- or double-stranded form, and unless specifically limited, encompasses known analogues of natural nucleotides that hybridize to nucleic acids in a manner similar to naturally occurring nucleotides. Unless otherwise indicated, a particular reference nucleic acid sequence implicitly encompasses conservatively modified variants thereof (i.e., sequence variants that hybridize with the reference nucleic acid, that encode the same amino acid sequence as the reference nucleic acid, or that encode amino acid sequences containing conservative amino acid substitutions as compared to the amino acid sequence encoded by the reference nucleic acid), and complementary sequences and as well as the sequence explicitly indicated.

The term "wild type," when applied to a gene, nucleic acid or gene product, especially a protein and/or biological property, denotes a gene, gene product, protein, or biological property predominantly found in nature. "Mutant" proteins, nucleic acids and the like occur less frequently and are often associated with loss or alteration of biological activity and a diseased state.

The term "dihydropyrimidine dehydrogenase gene" refers to a naturally occurring nucleic acid that encodes a protein that has dihydropyrimidine dehydrogenase activity, or that is specifically recognized by antibodies specific for dihydropyrimidine dehydrogenase. The term encompasses both wild-type and mutant genes.

"Intron-exon boundary" denotes a sequence of a gene present in or derived from a genomic DNA, wherein the sequence comprises intron sequences that are absent in a mature mRNA transcript, contiguous to exon regions that are present in the mature mRNA transcript.

A "splicing defect" is a failure to correctly remove an intron or to correctly connect two exons in the mature mRNA transcript, which often are the result of sequence mutations in the intron-exon boundary.

"Stringency" relates to the conditions under which hybridization and annealing take place. Low stringency hybridization and annealing conditions permit the annealing of complementary nucleic acids that contain mismatched nucleic acids. As the stringency is raised, annealing of sequences containing mismatched nucleic acids is disfavored. Conditions which result in low or high stringency levels are known in the art (e.g., increasing the annealing temperature raises the stringency).

An extensive guide to the hybridization of nucleic acids is found in Tijssen (1993) *Laboratory Techniques in Biochemistry and Molecular Biology—Hybridization with Nucleic Acid Probes* part I chapter 2 "overview of principles of hybridization and the strategy of nucleic acid probe assays", Elsevier, New York. Generally, highly stringent hybridization and wash conditions are selected to be about 5° C. lower than the thermal melting point ($T_m$) for the specific sequence at a defined ionic strength and ph. The $T_m$ is the temperature (under defined ionic strength and pH) at which 50% of the target sequence hybridizes to a perfectly matched probe. Very stringent conditions are selected to be equal to the $T_m$ for a particular probe.

Methods of alignment of sequences for comparison and determination of whether two sequences bind the same target are well known in the art. Optimal alignment of sequences for comparison may be conducted by the local homology algorithm of Smith and Waterman (1981) *Adv. Appl. Math.* 2: 482; by the homology alignment algorithm of Needleman and Wunsch (1970) *J. Mol. Biol.* 48: 443; by the search for similarity method of Pearson and Lipman (1988) *Proc. Natl. Acad. Sci. USA* 85: 2444; by computerized implementations of these algorithms (including, but not limited to CLUSTAL in the PC/Gene program by Intelligenetics, Mountain View, Calif., GAP, BESTFIT, FASTA, and TFASTA in the Wisconsin Genetics Software Package, Genetics Computer Group (GCG), 575 Science Dr., Madison, Wis., USA); the CLUSTAL program is well described by Higgins and Sharp (1988) *Gene,* 73: 237-244 and Higgins and Sharp (1989) *CABIOS* 5: 151-153; Corpet, et al. (1988) *Nucleic Adds Research* 16, 10881-90; Huang, et al. (1992) *Computer Applications in the Biosciences* 8, 155-65, and Pearson, et al. (1994) *Methods in Molecular Biology* 24, 307-31. Alignment is also often performed by inspection and manual alignment.

Figure 1A:
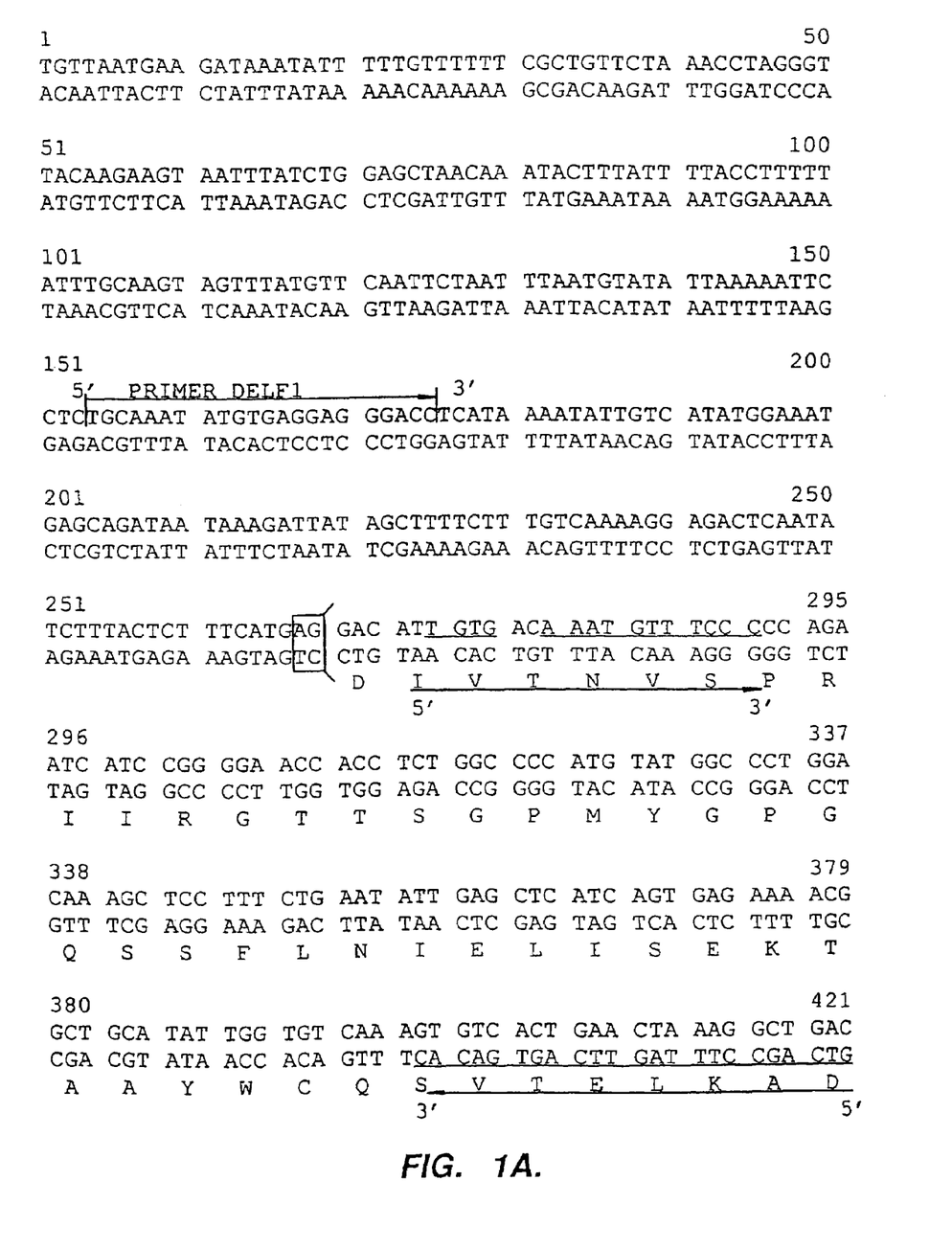
FIG. 1 provides genomic sequence from the DPD gene in the region of a splicing mutant which leads to the loss of an exon in the mRNA which encodes the amino acid sequence of SEQ ID NO:2. The primer binding sites for DELF-1 and DELR1 are indicated. The primer binding site for DPD15F and DPD15R (see, Meinsma et al. (1995) *DNA and Cell Biology* 14(1): 1-6) are also indicated. The Mae II site at the 3' splice junction is indicated. Inca mutant form, the G nucleotide at the 3' splice junction (residue 434) is mutated to an A nucleotide.
Figure 1B:
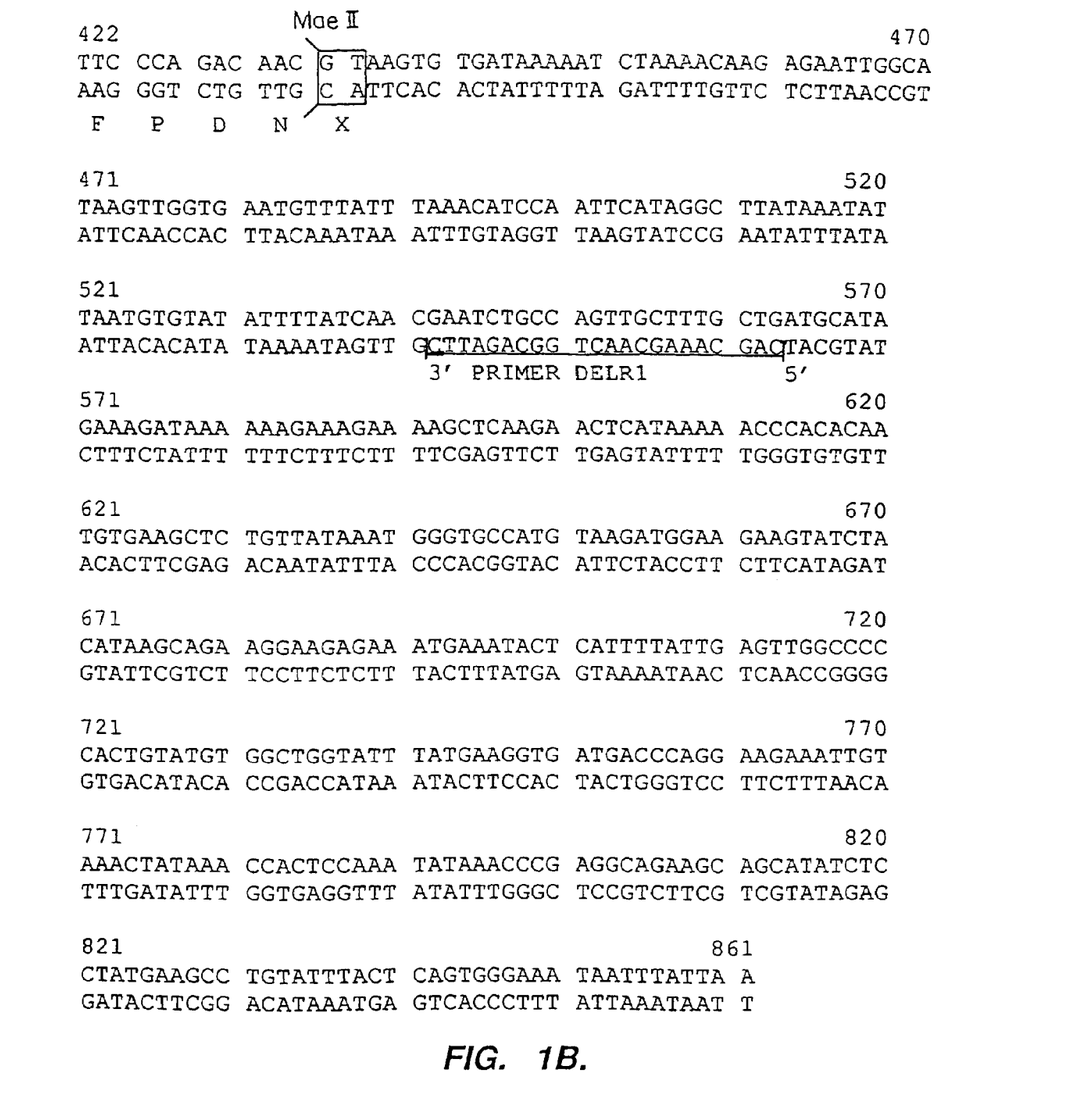

A "restriction endonuclease which recognizes a Mae II cleavage site" is a DNA endonuclease that recognizes and cleaves a nucleic acid which is cleaved by the restriction endonuclease Mae II (see also, FIG. 1).

A "PCR primer" is one of a pair of oligonucleotides complementary to a subregion of a nucleic acid that, when annealed to the nucleic acid, generates a double stranded sequence which supports nucleic acid synthesis by primer extension in a PCR reaction.

DETAILED DISCUSSION OF THE INVENTION

The present invention provides compositions, methods and kits for detecting point mutations in DPD nucleic acid samples. Genetic amplification techniques are used to detect point mutations in a splicing region of the DPD gene which results in the deletion of an exon in the DPD gene product, and causes one form of DPDD (DPD deficiency).

Isolation of Nucleic Acid Samples

To amplify a target intron-exon boundary in a sample, the nucleic acid encoding the sequence is made accessible to the components of the amplification system. In general, this accessibility is ensured by isolating the nucleic acids from the sample, however, isolation is optional (methods for amplifying nucleic acids, e.g., by PCR from whole cells are known and appropriate). A variety of techniques for extracting nucleic acids from biological samples are known in the art. For example, see those described in Rotbart et at., 1989, in *PCR Technology* (Erlich ed., Stockton Press, New York) and Han et al., 1987, *Biochemistry* 26:1617-1625. The methods described by Fries et al., *Am. J. Med. Genet.,* 46:363-368 (1993), are also useful.

Nucleic acids are isolated from cell or tissue samples from patients, and from cell culture. The culture of cells used in conjunction with the present invention, including cell lines and cultured cells from tissue or blood samples, including stem cells is well known in the art. Freshney (*Culture of Animal Cells, a Manual of Basic Technique,* third edition Wiley-Liss, New York (1994)) and the references cited therein provides a general guide to the culture of cells. See also, Kuchler et al. (1977) *Biochemical Methods in Cell Culture and Virology,* Kuchler, R. J., Dowden, Hutchinson and Ross, Inc, and Inaba et al. (1992) *J. Exp. Med.* 176, 1693-1702.

The methods of the present invention are employed for analyzing nucleic acid from a variety of different tissues, such as tissues samples (e.g., fetal and amniotic fluid tissue) and patient-derived tissue culture cell lines (e.g., fibroblast cell lines). Where blood cells are used, whole blood should be drawn with an anticoagulant in a sealed vacuum tube kept separated from other samples and handled with clean gloves. For best results, blood is processed immediately after collection; if this is impractical, it is kept in a sealed container until use. Cells in other physiological fluids, such as amniotic fluid, are also optionally assayed. When using any of these fluids, the cells in the fluid are typically separated from the fluid component by centrifugation.

Several methods are particularly well suited for use in amplifying target regions. The choice between these methods is typically governed by the size of the sample which is available for testing. One method is crude extraction which is useful for relatively large samples. Briefly, mononuclear cells from samples of blood, buffy coat, amniocytes from amniotic fluid, cultured chorionic villus cells, or the like are isolated by standard procedures (see, Freshney, supra). If testing is not performed immediately after sample collection, aliquots of cells can be pelletted in sterile Eppendorf tubes and the dry pellet frozen at −20° C. or colder until use.

The blood cells are resuspended (typically from 10 to about 10 nucleated cells per 100 µl to 1 ml) in a buffer of 50 mM Tris-HCl (pH 8.3), 50 mM KCl 1.5 mM MgCl$_2$, 0.5% Tween 20, 0.5% NP40 supplemented with 100 µg/ml of proteinase K. After incubating at 56° C. for 2 hr, the cells are heated to 95° C. for 10 min to inactivate the proteinase K and immediately moved to wet ice (snap-cool). If gross aggregates are present, another cycle of digestion in the same buffer should be undertaken. Ten µl of this extract is generally used for amplification.

When extracting DNA from tissues, e.g., chorionic villus cells or confluent cultured cells, the amount of the above mentioned buffer with proteinase K varies according to the size of the tissue sample. The extract is incubated for 4-10 hrs at 50°-60° C. and then at 95° C. for 10 minutes to inactivate the proteinase. During longer incubations, fresh proteinase K should be added after about 4 hr at the original concentration.

When the sample contains a small number of cells, extraction may be accomplished, e.g., by methods as described in Higuchi, "Simple and Rapid Preparation of Samples for PCR", in *PCR Technology,* Ehrlich, H. A. (ed.), Stockton Press, New York, which is incorporated herein by reference.

A relatively easy procedure for extracting DNA for amplification is a "salting out" procedure adapted from the method described by Miller et al., *Nucleic Acids Res.*, 16:1215 (1988). Mononuclear cells are separated on a Ficoll-Hypaque gradient. The cells are resuspended in 3 ml of lysis buffer (10 mM Tris-HCl, 400 mM NaCl, 2 mM $Na_2EDTA$, pH 8.2). Fifty µl of a 20 mg/ml solution of proteinase K and 150 µl of a 20% SDS solution are added to the cells and then incubated at 37° C. overnight. Rocking the tubes during incubation will improve the digestion of the sample. If the proteinase K digestion is incomplete after overnight incubation (fragments are still visible), an additional 50 µl of the 20 mg/ml proteinase K solution is mixed in the solution and incubated for another night at 37° C. on a gently rocking or rotating platform. Following adequate digestion, one ml of a 6M NaCl solution is added to the sample and vigorously mixed. The resulting solution is centrifuged for 15 minutes at 3000 rpm. The pellet contains the precipitated cellular proteins, while the supernatant contains the DNA. The supernatant is removed to a 15 ml tube that contains 4 ml of isopropanol. The contents of the tube are mixed gently until the water and the alcohol phases have mixed and a white DNA precipitate has formed. The DNA precipitate is removed and dipped in a solution of 70% ethanol and mixed gently. The DNA precipitate is removed from the ethanol and air dried. The precipitate is placed in distilled water and dissolved.

Kits are also commercially available for the extraction of high-molecular weight (i.e., genomic) DNA. These kits include Genomic Isolation Kit A.S.A.P. (Boehringer Mannheim, Indianapolis, Ind.), Genomic DNA Isolation System (GIBCO BRL, Gaithersburg, Md.), Elu-Quik DNA Purification Kit (Schleicher & Schuell, Keene, N.H.), DNA Extraction Kit (Stratagene, La Jolla, Calif.), TurboGen Isolation Kit (Invitrogen, San Diego, Calif.), and the like. Use of these kits according to the manufacturer's instructions is generally acceptable for purification of DNA when practicing the methods of the present invention.

The concentration and purity of the extracted DNA may be determined by spectrophotometric analysis of the absorbance of a diluted aliquot at 260 nm and 280 nm. Either 10 µl of crude extract, or 1 µg of purified DNA by the alternate methods are used for amplification.

PCR Amplification of the Intron-Exon Boundaries of the DPD Gene

The nucleic acids at intron-exon boundaries are typically amplified when determining whether a splicing defect is present in a sample. In a preferred embodiment, amplification is performed by the PCR method. Although the PCR process is well known in the art (see, U.S. Pat. Nos. 4,683,195; 4,683,202; and 4,965,188, each of which is incorporated herein by reference) and although commercial vendors, such as Roche Molecular Systems, sell PCR reagents and publish PCR protocols, some general PCR information is provided below for purposes of clarity and full understanding of the invention for those unfamiliar with the PCR process.

In brief, a DNA sample is heat denatured to separate the individual complementary strands and annealed in the presence a pair of oligonucleotide primers which are complementary to sequences present on opposite stands and located on either side of the sequence to be detected. The PCR mixture is then subjected to repeated cycles of DNA synthesis, denaturation and reannealing.

The first step of each cycle of the PCR involves the separation of the nucleic acid duplex formed by the primer extension. Once the strands are separated, the next step in PCR involves hybridizing the separated strands with primers that flank the target sequence. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid.

In a preferred embodiment of the PCR process, strand separation is achieved by heating the reaction to a sufficiently high temperature for an sufficient time to cause the denaturation of the duplex but not to cause an irreversible denaturation of the polymerase (see U.S. Pat. No. 4,965,188). Typical heat denaturation involves temperatures ranging from about 80° C. to 105° C. for times ranging from seconds to minutes. Strand separation, however, can be accomplished by any suitable denaturing method including physical, chemical, or enzymatic means. Strand separation may be induced by a helicase, for example, or an enzyme capable of exhibiting helicase activity. For example, the enzyme RecA has helicase activity in the presence of ATP. The reaction conditions suitable for strand separation by helicases are known in the art (see Kuhn Hoffman-Berling, 1978, *CSH*-Quantitative Biology 43:63-67; and Radding, 1982, *Ann. Rev. Genetics* 16:405-436, both of which are incorporated herein by reference).

Template-dependent extension of primers in PCR is catalyzed by a polymerizing agent in the presence of adequate amounts of four deoxyribonucleoside triphosphates (typically dATP, dGTP, dCTP, and dTTP) in a reaction medium comprised of the appropriate salts, metal cations, and pH buffering system. Suitable polymerizing agents are enzymes known to catalyze template-dependent DNA synthesis. In some instances, DPD-encoding RNA may be used as the initial template for primer extension is RNA. Polymerizing agents suitable for synthesizing a complementary, DNA (cDNA) sequence from the RNA template are reverse transcriptase (RT), such as avian myeloblastosis virus RT, Moloney murine leukemia virus RT, or *Thermus thermophilus* (Tth) DNA polymerase, a thermostable DNA polymerase with reverse transcriptase activity marketed by Roche Molecular Systems Typically, the RNA template is heat degraded during the first denaturation step after the initial reverse transcription step leaving only DNA template. Suitable polymerases for use with a DNA template include, for example, *E. coli* DNA polymerase I or its Klenow fragment, $T_4$ DNA polymerase, Tth polymerase, and Taq polymerase, a heat-stable DNA polymerase isolated from *Thermus aquatics* and commercially available from Roche Molecular Systems The latter enzyme is widely used in the amplification and sequencing of nucleic acids. The reaction conditions for using Taq polymerase are known in the art and are described in Innis, supra.

When RNA is amplified, an initial reverse transcription (RT) step is carried out to create a DNA copy (cDNA) of the RNA. PCT patent publication No. WO 91/09944, published Jul. 11, 1991, incorporated herein by reference, describes high-temperature reverse transcription by a thermostable polymerase that also functions in PCR amplification. High-temperature RT provides greater primer specificity and improved efficiency. A "homogeneous RT-PCR" in which the same primers and polymerase suffice for both the reverse transcription and the PCR amplification steps, and the reaction conditions are optimized so that both reactions occur without a change of reagents is also available. *Thermus ther-*

*mophilus* DNA polymerase, a thermostable DNA polymerase that can function as a reverse transcriptase, is used for all primer extension steps, regardless of template. Both processes can be done without having to open the tube to change or add reagents; only the temperature profile is adjusted between the first cycle (RNA template) and the rest of the amplification cycles (DNA template).

The PCR method can be performed in a stepwise fashion, where after each step new reagents are added, or in a fashion where all of the reagents are added simultaneously, or in a partial stepwise fashion, where fresh or different reagents are added after a given number of steps. For example, if strand separation is induced by heat, and the polymerase is heat-sensitive, then the polymerase is added after every round of strand separation. However, if, for example, a helicase is used for denaturation, or if a thermostable polymerase is used for extension, then all of the reagents are added initially, or, alternatively, if molar ratios of reagents are of consequence to the reaction, the reagents may be replenished periodically as they are depleted by the synthetic reaction.

Those skilled in the art will know that the PCR process is most usually carried out as an automated process with a thermostable enzyme. In this process, the temperature of the reaction mixture is cycled through a denaturing region, a primer annealing region, and an extension reaction region. Alternatively, the annealing and extension temperature can be the same. Reverse transcriptase-PCR uses such a two-step temperature cycling. A machine specifically adapted for use with a thermostable enzyme is commercially available from Roche Molecular Systems.

Those skilled in the art will also be aware of the problems of contamination of a PCR by the amplified nucleic acid from previous reactions and nonspecific amplification. Methods to reduce these problems are provided in PCT patent application Ser. No. 91/05210, filed Jul. 23, 1991, incorporated herein by reference. The method allows the enzymatic degradation of any amplified DNA from previous reactions and reduces nonspecific amplification. The PCR amplification is carried out in the presence of dUTP instead of dTTP. The resulting double-stranded, uracil-containing product is subject to degradation by uracil N-glycosylase (UNG), whereas normal thymine-containing DNA is not degraded by UNG. Adding UNG to the amplification reaction mixture before the amplification is started degrades all uracil-containing DNA that might serve as target. Because the only source of uracil-containing DNA is the amplified product of a previous reaction, this method effectively sterilizes the reaction mixture, eliminating the problem of contamination from previous reactions (carry-over). UNG itself is rendered temporarily inactive by heat, so the denaturation steps in the amplification procedure also serve to inactivate the UNG. New amplification products, therefore, though incorporating uracil, are formed in an effectively UNG-free environment and are not degraded.

Those practicing the present invention should note that, although the preferred embodiment incorporates PCR amplification, amplification of target sequences ir a sample may be accomplished by any known method, such as ligase chain reaction (LCR), transcription amplification, and self-sustained sequence replication, each of which provides sufficient amplification so that the target sequence can be detected by nucleic acid hybridization to a probe. Persons of skill will appreciate that in methods such as LCR, primers that are complementary to the specific polymorphism or mutation are used. In this instance amplification occurs when the polymorphism (i.e., point mutation) is present in the nucleic acid sample.

Alternatively, methods that amplify the probe to detectable levels can be used, such as Qβ-replicase amplification. The term "probe" encompasses, inter alia, the sequence specific oligonucleotides used in the above procedures; for instance, the two or more oligonucleotides used in LCR are "probes" for purposes of the present invention, even though some embodiments of LCR only require ligation of the probes to indicate the presence of an allele.

Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA) are found in Berger and Kimmel, *Guide to Molecular Cloning Techniques*, Methods in Enzymology volume 152 Academic Press, Inc., San Diego, Calif. (Berger); Sambrook at al. (1989) Molecular Cloning—A Laboratory Manual (2nd ed.) Vol. 1-3, Cold Spring Harbor Laboratory, Cold Spring Harbor Press, NY, (Sambrook); and Current Protocols in Molecular Biology, F. M. Ausubel et al., ads., Current Protocols, a joint venture between Greene Publishing Associates, Inc. and John Wiley & Sons, Inc., (1994 Supplement) (Ausubel), and in Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36-47; *The Journal Of NIH Research* (1991) 3, 81-94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077-1080; Van Brunt (1990) *Biotechnology* 8, 291-294; Wu and Wallace, (1989) *Gene* 4, 560; Barringer et al. (1990) *Gene* 89, 117, and Sooknanan and Malek (1995) *Biotechnology* 13: 563-564. Improved methods of cloning in vitro amplified nucleic acids are described in Wallace et al., U.S. Pat. No. 5,426,039.

The present invention provides, inter alia, a polymorphic form of DPD. In particular, the invention provides a DPDD polymorphism wherein the G at position 434 of the gene sequence shown in FIG. 1 is replaced by an A.

This particular polymorphism is detected by a variety of amplification techniques, preferably PCR as described supra. To detect this polymorphism by PCR, the PCR reaction is performed in the presence of primers that are complimentary to opposite strands of the genomic DNA, wherein the complementary sequences are located on either side of the point mutation. The precise sequences recognized by the primers are not critical. Typically, any pair of primers can be used as long as they (1) bracket the polymorphism, (2) are reasonably near to the polymorphism (while the primer binding sequence may be as far from the polymorphism as can support a PCR reaction, i.e., 1 to about 10 kb, it is preferable that the binding sequence be within about 500 nucleotides or less, and more preferable that the binding sequence be within 100 nucleotides of the exon-intron boundary to be assayed), and (3) bind the primers with an adequate degree of specificity. It is preferable that the sequence be unique to the gene of interest. Such sequences are identified by comparing sequences as described herein. Smaller primers have a higher probability of recognizing sites outside of the desired binding site, whereas very large primers are more expensive to make; generally, a primer of about 15-20 nucleotides is adequate, and therefore preferred.

Example primers used herein are DELF1, which hybridizes to nucleic acids corresponding to nucleotide 154 to nucleotide 175 of the DPD gene sequence, and DELR1, which hybridizes to nucleic acids corresponding to nucleotide 563 to nucleotide 542 of the DPD gene sequence as described in FIG. 1. It is important to note that other 15-20 nucleotide sequences within 500 nucleotides of the point mutation are also acceptable. Given the sequence of the affected exon, adjacent introns, and adjacent additional exons provided herein, selecting and making alternate primers is within the skill of a skilled practitioner in the relevant art.

The present invention also provides kits for the detection of genetic polymorphisms or mutations associated with DPDD. The kits comprise a vial containing amplification primers that span a DPDD-associated polymorphism or mutation in the gene encoding DPD. For example, the vial optionally contains DELF-1 and DELR-1. The kits optionally contain a vial containing a thermostable polymerase, genetic size markers for gels, amplification reagents, instructions and the like.

Sequence Analysis of Amplification Products

A variety of methods are employed to analyze the nucleotide sequence of the amplification products. Several techniques for detecting point mutations following amplification by PCR have been described in Chehab et al., *Methods in Enzymology*, 216:135-143 (1992); Maggio et al., *Blood*, 81(1):239-242 (1993); Cai and Kan, *Journal of Clinical Investigation*, 85(2):550-553 (1990) and Cai et al., *Blood*, 73:372-374 (1989).

One particularly useful technique is analysis of restriction enzyme sites following amplification. In this method, amplified nucleic acid segments are subjected to digestion by restriction enzymes. Identification of differences in restriction enzyme digestion between corresponding amplified segments in different individuals identifies a point mutation. Differences in the restriction enzyme digestion is commonly determined by measuring the size of restriction fragments by electrophoresis and observing differences in the electrophoretic patterns. Generally, the sizes of the restriction fragments is determined by standard gel electrophoresis techniques as described in Sambrook, and, e.g., in Polymeropoulos et al., *Genomics*, 12:492-496 (1992).

The size of the amplified segments obtained from affected and normal individuals and digested with appropriate restriction enzymes are analyzed on agarose or polyacrylamide gels. Because of the high discrimination of the polyacrylamide gel electrophoresis, differences of small magnitude are easily detected. Other mutations resulting in DPDD-related polymorphisms of DPD encoding genes also add unique restriction sites to the gene that are determined by sequencing DPDD-related nucleic acid sequences and comparing them to normal sequences.

Another useful method of identifying point mutations in PCR amplification products employs oligonucleotide probes specific for different sequences. The oligonucleotide probes are mixed with amplification products under hybridization conditions. Probes are either RNA or DNA oligonucleotides and optionally contain not only naturally occurring nucleotides but also analogs such as digoxygenin dCTP, biotin dCTP, 7-azaguanosine, azidothymidine, inosine, or uridine. The advantage of using nucleic acids comprising analogs include selective stability, resistance to nuclease activity, ease of signal attachment, increased protection from extraneous contamination and an increased number of probe-specific colored labels. For instance, in preferred embodiments, oligonucleotide arrays are used for the detection of specific point mutations as described below.

Probes are typically derived from cloned nucleic acids, or are synthesized chemically. When cloned, the isolated nucleic acid fragments are typically inserted into a replication vector, such as lambda phage, pBR322, M13, pJB8, c2RB, pcos1EMBL, or vectors containing the SP6 or 17 promoter and cloned as a library in a bacterial host. General probe cloning procedures are described in Arrand J. E., *Nucleic Acid Hybridization A Practical Approach*, Hames B. D., Higgins, S. J., Eds., IRL Press 1985, pp. 17-45 and Sambrook, J., Fritsch, E. F., Maniatis, T., *Molecular Cloning A Laboratory Manual*, Cold Spring Harbor Press, 1989, pp. 2.1-3.58, both of which are incorporated herein by reference.

Oligonucleotide probes and primers are synthesized chemically with or without fluorochromes, chemically active groups on nucleotides, or labeling enzymes using commercially available methods and devices like the Model 380B DNA synthesizer from Applied Biosystems, Foster City, Calif., using reagents supplied by the same company. Oligonucleotides for use as probes, e.g., in in vitro amplification methods, or for use as gene probes are typically synthesized chemically according to the solid phase phosphoramidite triester method described by Beaucage and Caruthers (1981), *Tetrahedron Letts.*, 22(20):1859-1862, e.g., using an automated synthesizer, as described in Needham-VanDevanter et al. (1984) *Nucleic Acids Res.*, 12:6159-6168. Oligonucleotides can also be custom made and ordered from a variety of commercial sources known to persons of skill. Purification of oligonucleotides, where necessary, is typically performed by either native acrylamide gel electrophoresis or by anion-exchange HPLC as described in Pearson and Regnier (1983) *J. Chrom.* 255:137-149. The sequence of the synthetic oligonucleotides can be verified using the chemical degradation method of Maxam and Gilbert (1980) in Grossman and Moldave (eds.) Academic Press, New York, *Methods in Enzymology* 65:499-560.

Oligonucleotide probes and primers are selected using commercially available computer programs to compare known DNA sequences from gene sequences found in gene libraries, such as Genebank and EMBL, and the sequences described herein. The programs identify unique nucleotide sequences within the gene of interest. One such program is Eugene. Oligonucleotide sequences for PCR of a unique genomic DNA such as a chromosome subsequence are chosen optimally by choosing sequences according to previously established protocols or by computer programs that choose the degree of homology desired along with the length of the probe. Sequences are chosen to avoid technical problems such as primer dimers resulting from amplification of hybridized primers.

Primers and probes are optionally labeled with fluorophores or enzymes that generate colored products. This allows simultaneous use of probes to different DPDD-related polymorphisms or mutations. Identification of hybridization of a specifically labelled primer provides a means for determining which polymorphism or mutation is present in the nucleic acid of the sample. The primers used in the assay are labeled with more than one distinguishable fluorescent or pigment color. Primers are labeled with Texas red, rhodamine and its derivatives, fluorescein and its derivatives, dansyl, umbelliferone and the like or with horse radish peroxidase, alkaline phosphatase, biotin, avidin, or the like.

Primers and probes are labeled directly or indirectly. The common indirect labeling schemes covalently bind a ligand to the nucleotide and prepare labeled probe by incorporating the ligand using random priming or nick translation. The ligand then binds an anti-ligand which is covalently bound to a label. Ligands and anti-ligands vary widely. When a ligand has an anti-ligand, e.g., biotin, thyroxine, or cortisol, the ligand is used in conjunction with the labelled naturally-occurring anti-ligand. Alternatively, a hapten or antigen may be used in combination with an antibody, which is optionally labeled.

Sequence specific oligonucleotide probes hybridize specifically with a particular segment of the target polymorphism or mutation amplification products and have destabilizing mismatches with the sequences from other polymorphisms or mutations. Under sufficiently stringent hybridization conditions, the probes hybridize specifically only to exactly complementary sequences. The stringency of the hybridization conditions can be relaxed to tolerate varying amounts of sequence mismatch. Detection of the amplified product utilizes this sequence-specific hybridization to insure detection of only the correct amplified target, thereby decreasing the chance of a false positive caused by the presence of homologous sequences from related polymorphisms or mutations.

Specific DPD-encoding polymorphisms or mutations are also identified by sequencing the amplification products or restriction fragments thereof. Sequencing is performed by a variety of methods well known in the art. For example, the sequence of the amplified nucleic acid segments may be determined by the Maxam-Gilbert chemical degradation method as described in Sambrook. Generally, Sanger dideoxy-mediated sequencing is employed as described in Sambrook, or sequencing by hybridization is performed as described below.

Detection of Splicing Site Defects Using Nucleic Acid Arrays

In one preferred class of embodiments, splicing site defects at intron-exon boundaries are detected by hybridization of amplification products which include the splicing site to oligonucleotide arrays which discriminate single base-pair mismatches. In this embodiment, primers are used to amplify an intron-exon boundary in a PCR reaction, resulting in PCR amplicons which comprise the intron-exon boundary. The sequence of the entire PCR amplicon, or any subsequence thereof can be determined by labeling the PCR amplicon (typically with biotin or a fluorescent label) and hybridization to an array of oligonucleotide probes. In these hybridization methods single base pair mismatches in labeled nucleic acids to probes in the array are distinguished.

Preferably in this class of embodiments, the oligonucleotide arrays are designed to sequence nucleic acids at the intron-exon boundary. More preferably, the arrays are designed to discriminate whether a particular nucleotide is altered relative to the wild-type sequence. This is done by constructing an array with two or more oligonucleotide probe sets which differ by a single nucleotide. Hybridization to the known probe sequence by a target nucleic acid under conditions where a single mismatch does not bind indicates the presence of a fully complementary nucleic acid.

Sequencing by hybridization to arrays of oligonucleotides is described in U.S. Pat. No. 5,202,231, to Drmanac et al. and, e.g., in Drmanac et al. (1989) Genomics 4:114-128. Methods of constructing and designing arrays for sequencing and detection of single nucleotide alterations is known in the art. The development of very large scale immobilized polymer synthesis (VLSIPS™) technology provides methods for arranging large numbers of oligonucleotide probes for the detection and sequencing of nucleic acids in very small arrays. See, WO 90/15070 and 92/10092; Pirrung et al., U.S. Pat. No. 5,143,854 (see also PCT Application No. WO 90/15070); McGall et al., U.S. Pat. No. 5,412,087; and U.S. Pat. No. 5,384,261. See also, Fodor et al. (1991) Science, 251: 767-777 and Sheldon et al. (1993) Clinical Chemistry 39(4): 718-719. The oligonucleotide arrays are typically placed on a solid surface such as a glass slide with an area less than 1 inch$^2$, although much larger surfaces are optionally used.

Mechanical and Light directed oligonucleotide array construction methods are used for the construction of oligonucleotide arrays. Light directed methods are the most common, and are found, e.g., in U.S. Pat. No. 5,143,854. The light directed methods discussed in the '854 patent typically proceed by activating predefined regions of a substrate or solid support and then contacting the substrate with a preselected monomer solution. The predefined regions are activated with a light source, typically shown through a photolithographic mask. Other regions of the substrate remain inactive because they are blocked by the mask from illumination. Thus, a light pattern defines which regions of the substrate react with a given nucleic acid reagent. By repeatedly activating different sets of predefined regions and contacting different reagent solutions with the substrate, a diverse array of oligonucleotides is produced on the substrate. Other steps, such as washing unreacted reagent solutions from the substrate, are used as necessary.

The surface of a solid support is typically modified with linking groups having photolabile protecting groups and illuminated through a photolithographic mask, yielding reactive hydroxyl groups in the illuminated regions. For instance, during oligonucleotide synthesis, a 3'-O-phosphoramidite (or other nucleic acid synthesis reagent) activated deoxynucleoside (protected at the 5'-hydroxyl with a photolabile group) is then presented to the surface and coupling occurs at sites that were exposed to light in the previous step. Following capping, and oxidation, the substrate is rinsed and the surface illuminated through a second mask, to expose additional hydroxyl groups for coupling. A second 5'-protected, 3'O-phosphoramidite activated deoxynucleoside (or other monomer as appropriate) is then presented to the resulting array. The selective photodeprotection and coupling cycles are repeated until the desired set of oligonucleotides (or other polymers) is produced.

The PCR amplicons detected on the arrays are labeled with a composition detectable by spectroscopic, photochemical, biochemical, immunochemical, or chemical means. For example, useful labels include 32P, 35S, fluorescent dyes, chromophores, electron-dense reagents, enzymes (e.g., as commonly used in an ELISA), biotin, dioxigenin, or haptens and proteins for which antisera or monoclonal antibodies are available. In preferred embodiments, the label is detectable spectroscopically, i.e., is chromogenic. Suitable chromogens include molecules and compounds which absorb light in a distinctive range of wavelengths so that a color may be observed, or emit light when irradiated with radiation of a particular wavelength or wavelength range (e.g., a fluorescent label).

EXAMPLES

The following examples are offered by way of illustration and not limitation. One of skill will readily recognize a variety of parameters and conditions which can be changed or modified to yield essentially identical results.

The following example pinpoints a polymorphism or "mutation" of the gene encoding DPD that is associated with DPDD, and provides a novel method for the efficient detection of this DPDD splicing mutation.

Example 1

The PCR reaction is performed using human genomic DNA obtained from fibroblast cultures of 5 members of a family, one of which was afflicted with DPDD.

Figure 2:
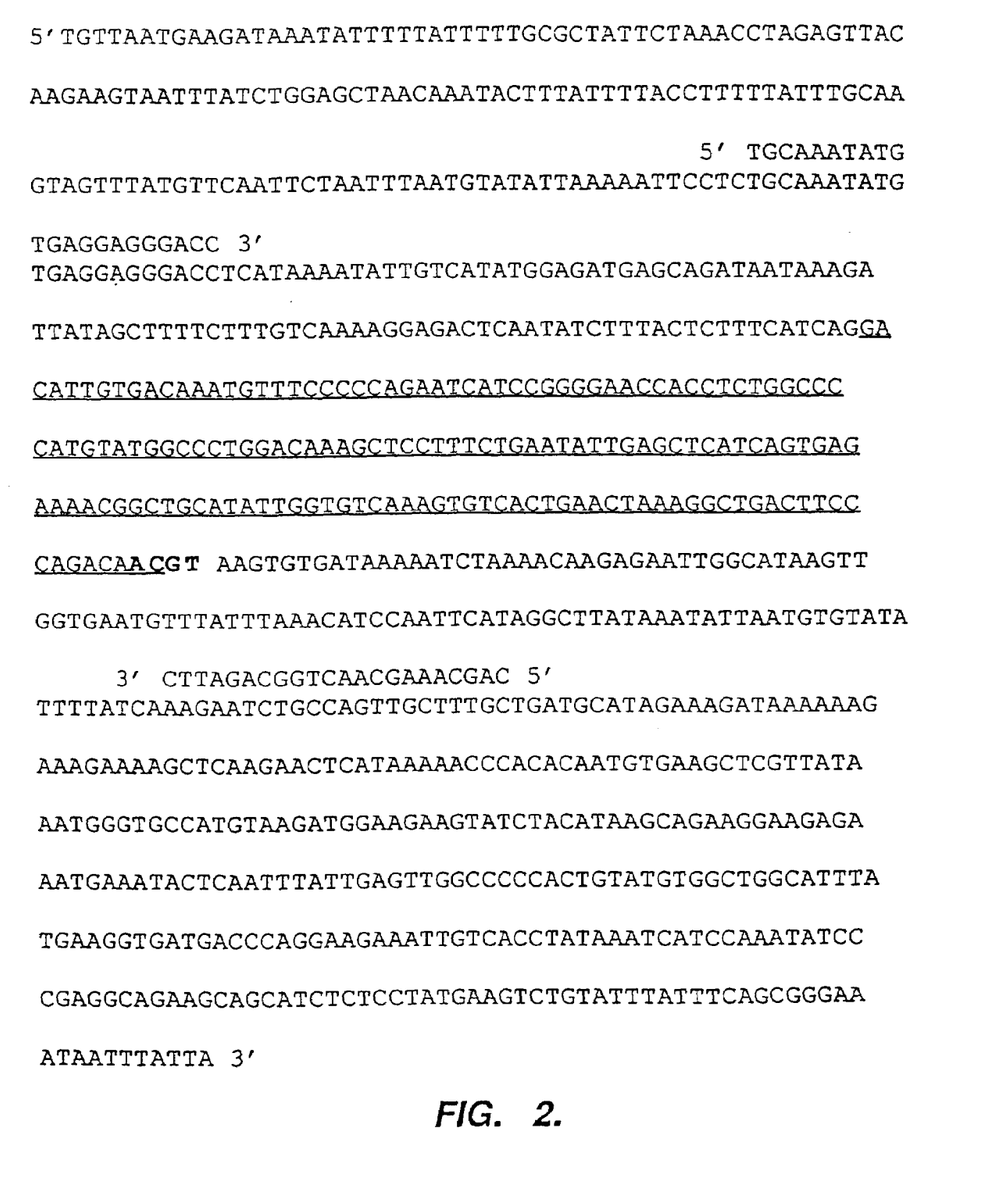
FIG. 2 provides further details of PCR reaction components for amplifying the region of a splicing site mutant (SEQ ID NO:7). The exon is underlined. The splice site which is polymorphic is in bold text. Primers DELF1 and DELR1 are indicated (SEQ ID NOS:5 and 6).

The PCR primers were selected so as to bracket the exon that is not present in the DPDD gene and part of the two introns on either side of this exon. Primers were synthesized using an Applied Biosystems 394 DNA & RNA synthesizer. The forward primer was DELF1, which encompassed nucleotide 154 to nucleotide 175 of the DPFD gene sequence and had the sequence TGCAAATATGTGAGGAGGGACC (SEQ ID NO:3)(see also FIG. 1 and FIG. 2). The reverse primer was DELR1, which encompassed nucleotide 563 to nucleotide 542 of the DPFD gene sequence and had the sequence CAAAGCAACTGGCAGATTC (SEQ ID NO:4)(see also FIG. 1 and FIG. 2). PCR was carried out in 50 μl of a reaction mixture consisting of 10 mM Tris HCl pH 8.3, 50 mM KCl, 2.5 mM $MgCl_2$, 0.5 mM dNTPs, 1 μM of each primer, and 2.5 units Taq polymerase (Roche Molecular Systems) for 30 cycles denaturing at 96° C. for 1 min, annealing at 55° C. for 1 min, and extending at 72° C. for 2 min. The amplified products were extracted with 1 volume of chloroform and purified by filtration through Centricon 100 filter units.

Typically, one-fifth of the purified PCR product was used for sequence analyses with an Applied Biosystems 373A automated sequencer and fluorescent dye-deoxy terminator chemistry. Sequence data were analyzed using the MacVector sequence analysis software (International Biotechnology).

The PCR fragments were analyzed by electrophoresis in a 1% agarose gel stained with ethidium bromide. For Southern blot analysis, the DNA in the gels were depurinated by a 20-min incubation in 200 mM HCl and denatured by a 20-min incubation in 0.5 M NaOH. The DNA was transferred to Gene Screen Plus nylon membranes (New England Nuclear) overnight in 0.5 M NaOH, and was fixed to the filter by baking for 90 min at 80° C. Prehybridization was done in a solution of 6×SSC, Denhardt's reagent, 0.5% $NaDodSO_4$, and 0.2 mg/ml sonicated salmon sperm DNA at 65° C. for 3 hr, then hybridization was carried out overnight at 65° C. in the same solution containing 1.5 z $10_6$ cpm/ml of $^{32}P$ random priming-labeled human DPD, cDNA. After washing at 65° C. for 20 min in 2×SSC, 0.5% $NaDodSO_4$, and 45 min in 0.1×SSC, 0.5% $NaDodSO_4$ at 65° C., the membranes were exposed to X-ray film (Eastman Kodak Co.) at –80° C. for 30 min.

The results of sequencing the various genomic DNAs reveal the presence of a G to A mutation at position 434. This mutation was located within the splice site. The DPDD patient was homozygous for this mutation. Both parents and one sibling were heterozygous and another was homozygous for the normal allele.

The G to A mutation resulted in the destruction of a restriction site recognized by restriction endonucleases which recognize the Mae II binding sequence, ACGT. Consequently, after PCR amplification of genomic DNA using the primers DELF1 and DELR1, digestion of the resulting PCR product with a restriction endonuclease that cleave the MaeII site yields fragments having the following sizes:

| Normal allele | Mutant allele |
|---|---|
| 278 + 131 bp | 408 bp |

Example 2

Identification of a Polymorphism Which Causes DPDD Family Pedigree

Blood samples from a British family were collected after a family member displayed excessive 5-FU toxicity during chemotherapy. This family is unrelated to any family with DPD deficiency that has previously been reported. To screen for the presence of the mutation leading to the deficiency in the normal population, genomic DNA was collected from healthy subjects representing the following ethnic groups: Caucasians (English and Finnish), Asians (Japanese and Taiwanese) and African-Americans. DPD catalytic activity.

DPD catalytic activity for the family under study was determined from peripheral blood mononuclear cells using a previously described HPLC method (McMurrough et al. (1996) *Br. J. Clin. Pharmacol.*). In brief, peripheral blood mononuclear cells were purified from the patient's blood in a density gradient using Ficoll-Hypaque (Pharmacia, Upsala) and incubated for 90 min with [$^{14}C$]-5 FU. The production of 5-FU metabolites were then quantified by HPLC analysis by radiodetection.

Isolation of RNA and RT-PCR.

Total RNA was isolated from peripheral blood mononuclear cells by the guanidinium thiocyanate-phenol-chloroform method (Chomezynski et al. (1987) *Anal. Biochem.* 162: 156-159). The RNA solutions were dissolved in DEPC-treated water and stored at –80° C. until use. RT-PCR was performed as described (Meinsma et al. (1995) *DNA Cell. Biol.* 14: 1-6) and the products were analyzed by electrophoresis in 0.8% agarose gels and visualized by staining with ethidium bromide.

Cloning and Characterization of the Genomic Fragment Encoding the Deleted Exon.

The DPD cDNA was used as a probe to isolate a P1 clone containing about 100 kbp of the human DPD gene (PAC 5945) from a high density PAC human genomic library (Genome Systems, St. Louis, Mo.). Southern blotting was used to confirm that the P1 clone contained the deleted exon using a probe located within the deleted fragment. This probe was synthesized from the DPD cDNA by using the primers: DPD15 (forward): 5' TTGTGACAAATGTTTCCC 3' (SEQ ID NO:5) and DPD15R (reverse): 5' AGTCAGCCTTTAGT-TCAGTGACAC 3' (SEQ ID NO:6) to specifically amplify the putative exon. PCR conditions were as indicated below but extension was carried out at 72° C. for 1 min. This PCR fragment was purified using a Wizard PCR purification kit (Promega, Madison, Wis.), labeled with [$\alpha^{32}P$]-dCTP and hybridized with the clone PAC 5945. DNA was purified from this genomic clone using Qiagen columns (Qiagen, Chatsworth, Calif.), and the 5' and 3' ends of the deleted exon and adjacent intronic regions were sequenced by chromosome walking from within the deleted exon using dideoxy terminator chemistry and an ABI 373A DNA sequencer (Applied Biosystems, Foster City, Calif.). The intronic sequences obtained allowed the selection of appropriate primers (e.g., delF1 and delR1) to amplify from genomic DNA the complete exon and immediate flanking intronic sequences. All primers used in this study were synthesized with a 391 DNA&RNA synthesizer (Applied Biosystems, Foster City, Calif.).

Genotyping of the Mutant DPD Allele.

A 409 bp PCR genomic fragment corresponding to the deleted exon (from G1822 to C1986 in Yokota, et al. (1994) *J. Biol. Chem.* 269: 23192-23196) plus the flanking intronic sequences containing the AG and GT splicing consensus sequences was amplified from human genomic DNA using the primers delF1 (forward) 5' TGCAAATATGTGAG-GAGGGACC 3' (SEQ ID NO:3) and delR1 (reverse) 5' CAG-CAAAGCAACTGGCAGATTC 3'(SEQ ID NO:4). PCR amplification was carried out in a 100 μl reaction mixture containing 10 mM Tris-HCl (pH 8.3), 50 mM KCl, 1.5 mM $MgCl_2$, 0.2 mM of each dNTP, 0.5 μM of each primer, 2.5 units of Taq Polymerase (Roche Molecular Systems) and 500 ng of genomic DNA template for 31 cycles by denaturing at 94° C. for 1 min, annealing at 60° C. for 1 min and extending at 72° C. for 2 min. Subjects identified as wild type, heterozygous or homozygous for the splicing mutation could be distinguished by digesting the PCR product with the restriction endonuclease Mae II (Boehringer, Mannheith, Indianapolis, Ind.) and electrophoresis in 1% regular, 3% NuSieve agarose gels (FMC Bioproducts, Rockland, Me.). The genotypes obtained were verified by sequencing the 409 bp PCR product. The sources of the genomic DNA samples for the different ethnic groups correspond to those previously described (Fernandez-Salguero et al. (1995) Am. J. Hum. Genet. 57: 651-660).

DPD Catalytic Activity.

To determine DPD catalytic activities in the proband and family members, lymphocytes were isolated and subjected to analysis by HPLC (McMurrough et al. (1996) Br. J. Clin. Pharmacol.). Activities ranged between 24% to 70% of the mean DPD activity determined in the normal population (155 pmole/min/mg protein) (Table 1). It should be noted that all the subjects in the pedigree presented a relatively low catalytic activity (below 70% of the mean in the normal population). Subject I1, a cancer patient who exhibited 5-FU toxicity, had catalytic activity which was 24% of the mean population.

RT-PCR Analysis.

Figure 3:
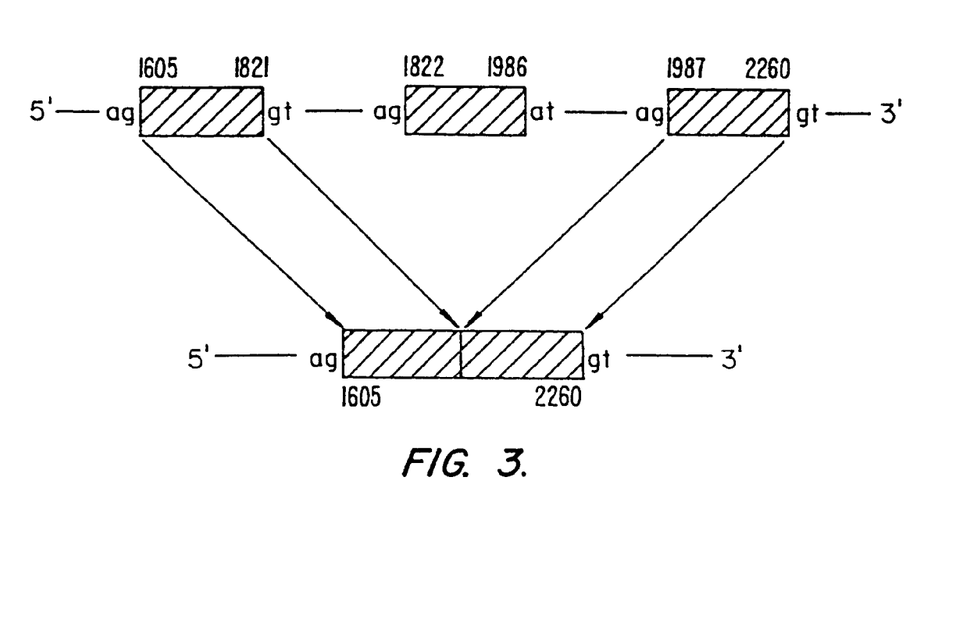
FIG. 3 is a schematic of the splicing product of the mutant DPD gene.

RT-PCR was performed on total RNA isolated from peripheral blood mononuclear cells corresponding to each of the members of the pedigree shown in FIG. 1. The full length coding region of the DPD cDNA was amplified in three fragments of 1.5 kbp, 906 bp and 919 bp. The 1.5 kbp and 906 bp PCR fragments were detected in all the members of the family and correspond to the normal mRNA as expected from the cDNA sequence. A 741 bp band corresponded to the deleted exon and was heterozygous with respect to the wild type 906 bp fragment. Sequencing of this 741 bp PCR fragment confirmed that a 165 bp deletion has occurred that precisely corresponds to that previously reported in a Dutch family (Meinsma et al. (1995) DNA Cell. Biol. 14: 1-6). No homozygous mutant subjects were found in this pedigree. The generation of the mutant mRNA is illustrated in FIG. 3. Faulty splicing is the mechanism for the generation of the shorter mRNA, which due to the absence of 55 amino acids would be unable to be translated into an intact DPD enzyme.

Genomic DNA Sequence Analysis of the Mutant DPD Allele.

A clone containing the deleted exon was isolated in a recombinant P1 phage. Sequence of the intronic regions flanking the deleted exon enabled the development of a PCR reaction to sequence the exon and across the 5' and 3' splicing sites. Sequence of the 409 bp PCR genomic fragment clearly indicated the presence of a G to A point mutation (GT to AT) at the 5' donor splice consensus sequence in the British pedigree in subjects I1, I2, I3, I4, I7, I8, I9, III6, III8 and III9. Subjects II1, II6, III1, III2, III4 and III7 were found to have two normal alleles. The subject previously reported to have the 165 bp deletion present in both alleles and his heterozygote brother (subjects 1 and 2 in Meinsma et al. reference) were also analyzed and found to possess the splicing mutation present in both alleles for subject 1 and in one allele for subject 2. The G to A mutation correlates 100% with the corresponding RT-PCR results for the deletion of the entire exon, indicating that the CT to AT mutation in the 5' splicing consensus sequence of the DPD gene leads to skipping of the entire preceding exon. The genotypes and catalytic activities for this 5'-splicing mutation in the pedigree are summarized in Table I.

Genotyping Test for the Mutant DPD Allele and Population Screening.

Figure 4:
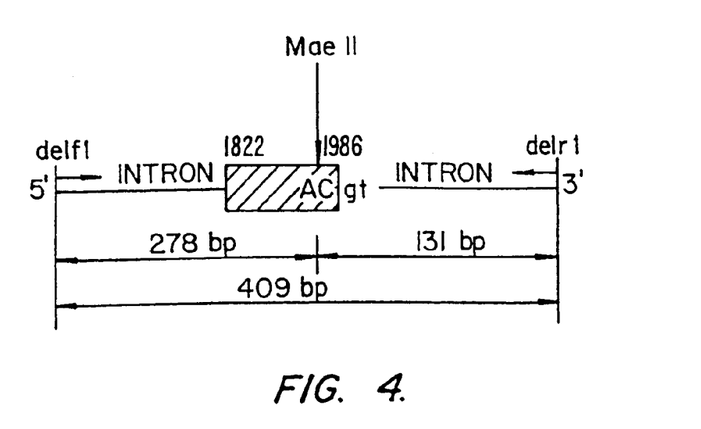
FIG. 4 is a schematic representation of an example strategy for amplifying an exon deleted in mutant Dpd mRNA from the genomic DNA for the gene. The restriction endonuclease Mae II produces fragments of 278 bp and 131 bp in the wild-type allele. A point mutation at the donor splicing consensus sequence (GT to AT) destroys the restriction site, and thus, the mutant form remains undigested (409 bp).

The 409 bp genomic PCR fragment containing the deleted exon has a restriction site for the endonuclease Mae II (A-CGT) which produces two fragments of 278 bp and 131 bp from the wild type allele. This site is eliminated when a G to A mutation occurs at the 5'-splicing site (A-CAT). A diagrammatic representation of the strategy developed for PCR amplification of the 409 bp fragment and the restriction enzyme pattern expected with MAE II is shown in FIG. 4. The reliability of the genotyping assay was confirmed by sequencing the 409 bp PCR product in these samples. By analyzing normal subjects within different ethnic groups (Table II), we found that this mutant allele is present in the Finnish (4.4%) and Taiwanese (5.4%) populations where heterozygotes were detected. However, within the samples tested to date, no mutant alleles were found in 35 Japanese or 20 African-American subjects. All heterozygous subjects found by restriction enzyme analysis were also confirmed by genomic DNA sequence analysis.

TABLE I

Relationship between phenotype and genotype for the DPD catalytic activity and the presence of the 5'-splicing mutation in the pedigree analyzed.

| Family Member | DPD activity (%)* | Genotype[#] |
|---|---|---|
| I1 | 24 | +/− |
| II1 | 57 | +/+ |
| II2 | 39 | +/− |
| II3 | 36 | +/− |
| II4 | 42 | +/− |
| II5 | n/d | n/d |
| II6 | 35 | +/+ |
| II7 | 58 | +/− |
| II8 | 22 | +/− |
| II9 | 28 | +/− |
| III1 | 55 | +/+ |
| III2 | 60 | +/+ |
| III3 | n/d | n/d |
| III4 | 60 | +/+ |
| III5 | n/d | n/d |
| III6 | 36 | +/− |
| III7 | 70 | +/+ |
| III8 | 31 | +/− |
| III9 | 56 | +/− |

*DPD activity is expressed as percentage of the mean activity in the normal population.
[#]Genotype for the GT to AT splice mutation: +/+: wild type; +/−: heterozygote; /: homozygote; n/d: not determined

TABLE II

Allelic frequency for the presence of the 5'-splicing mutation in different ethnic groups from the normal population

| | Subject* | Wild type (+/+) | Heterozygote (+/−) | Homozygote (−/−) |
|---|---|---|---|---|
| Caucasian | | | | |
| British | 30 | 100 (30)[a] | 0 (0)[a] | 0 (0)[a] |
| Finnish | 45 | 95.6 (43) | 4.4 (2) | 0 (0) |
| Asian | | | | |
| Taiwanese | 37 | 94.6 (35) | 5.4 (2) | 0 (0) |
| Japanese | 35 | 100 (35) | 0 (0) | 0 (0) |

TABLE II-continued

Allelic frequency for the presence of the 5'-splicing mutation
in different ethnic groups from the normal population

| Subject* | Wild type (+/+) | Heterozygote (+/−) | Homozygote (−/−) |
|---|---|---|---|
| African-American | 20 | 100 (20) | 0 (0) | 0 (0) |

*The allelic frequency is indicated as a percentage of the total number of subjects analyzed.
The absolute number of heterozygote subjects are indicated in parenthesis.

All publications, patents and patent applications mentioned in this specification are herein incorporated by reference into the specification to the same extent as if each individual publication, patent or patent application was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

What is claimed is:

1. A method for detecting a splicing defect in a dihydropyrimidine dehydrogenase (DPD) gene from a human patient, wherein said method comprises determining whether a genomic DNA from the patient comprises the nucleic acid sequence of SEQ ID NO:1 or a variant of the nucleic acid sequence of SEQ ID NO:1 wherein said variant differs from the nucleic acid sequence of SEQ ID NO:1 by a conversion of the G residue at position 434 of SEQ ID NO:1 to an A residue and wherein the presence of the conversion indicates the presence of the splicing defect.

2. The method of claim 1, wherein genomic DNA comprising the conversion site at position 434 of SEQ ID NO:1 is amplified.

3. The method of claim 2, wherein the method comprises amplifying the genomic DNA with a primer which hybridizes to a nucleic acid having the sequence of SEQ ID NO:1.

4. The method of claim 2, wherein the amplified DNA is cleaved with a restriction endonuclease which recognizes a Mae II cleavage site.

5. The method of claim 1, wherein the residue at position 434 is determined using an oligonucleotide array.

6. A method for screening a human patient for sensitivity to 5-fluorouracil wherein the sensitivity is due to the conversion of a G residue to an A residue at position 434 in the nucleic acid sequence of SEQ ID NO:1, comprising isolating a genomic DNA from the patient which comprises the nucleic acid sequence of SEQ ID NO:1 or the variant thereof having the conversion and determining whether the isolated genomic DNA has the conversion, wherein the presence of the conversion indicates the presence of the sensitivity and the absence of the conversion indicates the absence of the sensitivity.

7. The method of claim 6, wherein the method comprises the step of amplifying genomic DNA comprising the conversion site at position 434 of SEQ ID NO:1.

8. The method of claim 7, wherein the method comprises amplifying the genomic DNA with a PCR primer which hybridizes to a nucleic acid having the sequence of SEQ ID NO:1.

9. The method of claim 7, wherein the amplified DNA is cleaved with a restriction endonuclease which recognizes a Mae II cleavage site.

10. A method for determining that a human patient has a splicing defect in a dihydropyrimidine dehydrogenase (DPD) gene that comprises SEQ ID NO:1, wherein the splicing defect is at the splice site of the DPD gene having nucleotides 432-435 of SEQ ID NO:1 (ACGT), wherein the splicing defect is a conversion of a G residue to an A residue at position 434 of SEQ ID NO:1, wherein said method comprises:
 (a) isolating genomic DNA comprising the ACGT splice site of the DPD gene from the human patient;
 (b) amplifying the isolated genomic DNA;
 (c) determining whether the amplified genomic DNA has the conversion;
 wherein the presence of the conversion indicates the human patient has the splicing defect.

11. A method for determining that a human patient does not have a splicing defect of a dihydropyrimidine dehydrogenase (DPD) gene that comprises SEQ ID NO:1, wherein the splicing defect is at the splice site of the DPD gene having nucleotides 432-435 of SEQ ID NO:1 (ACGT), wherein the splicing defect is a conversion
of the G residue to an A residue at position 434 of SEQ ID NO:1, wherein said method comprises:
 (a) isolating genomic DNA comprising the ACGT splice site of the DPD gene from the human patient;
 (b) amplifying the isolated genomic DNA;
 (c) determining whether the amplified genomic DNA has the conversion in the splice site,
 wherein the presence of the conversion indicates that the human patient has the splicing defect.

* * * * *